United States Patent [19]

Schroeder et al.

[11] 4,197,247

[45] Apr. 8, 1980

[54] REMOVAL OF BROMINE FROM PHTHALIC ANHYDRIDE

[76] Inventors: Hobe Schroeder, 30 W. 110 Lindenwood Ct., Warrenville, Ill. 60555; Delbert H. Meyer, 1524 Clyde Dr., Naperville, Ill. 60540

[21] Appl. No.: 21,342

[22] Filed: Mar. 19, 1979

[51] Int. Cl.² ............................................. C07D 307/89
[52] U.S. Cl. ................................ 260/346.7; 260/346.4
[58] Field of Search ........................... 260/346.4, 346.7

[56] References Cited

U.S. PATENT DOCUMENTS 2,670,325  2/1954  West et al. ................... 260/346.7 X Primary Examiner—Richard Raymond

[57] ABSTRACT

Bromine-substituted oxygen-containing impurities in phthalic anhydride which cannot be removed therefrom by distillation or a combination of heat treatment in the presence of a metal or a combination of catalytic hydrogenation and fractional distillation are removed by treating a mixture of vapors of such impure phthalic anhydride and water with a palladium catalyst prior to taking phthalic anhydride as a product fraction of fractional distillation.

5 Claims, No Drawings

REMOVAL OF BROMINE FROM PHTHALIC ANHYDRIDE

FIELD OF THE INVENTION

This invention relates to the purification of phthalic anhydride and more specifically pertains to the removal from said anhydride of bromine, generally present as bromine-substituted oxygen-containing aromatic compounds having boiling point temperatures at close to the boiling point temperature of said anhydride.

BACKGROUND OF THE INVENTION

Phthalic anhydride can be obtained from oxidation of o-xylene with air both in the vapor phase in the presence of a vanadium catalyst promoted by hydrogen bromide as disclosed by U.S. Pat. No. 2,954,385 or in the liquid phase in the presence of cobalt, or manganese or cobalt and manganese in combination with a source of bromine as disclosed by British Patent Specification No. 856,245; U.S. Pat. No. 3,402,184; a copending U.S. patent application Ser. No. 867,050 filed Jan. 3, 1978 and Ser. No. 961,763 filed Nov. 17, 1978. The processes of the last patent applications yield a phthalic acid product which is separated from the metal components of catalysis and other high boiling impurities by dehydration to and evaporation of a partially purified anhydride. All of such obtained phthalic anhydride products contain bromine-substituted oxygen-containing compounds and low molecular weight bromine-containing compounds which in general are readily removed by a selective condensation of a vapor-gas mixture in a partial purification step. The bromine and oxygen-containing aromatic compounds are more difficult to remove from partially purified phthalic anhydride because such bromo compounds have physical characteristics; e.g., vapor pressure, rather close to the physical characteristics of the anhydride.

Insofar as we are aware, there is no prior art directed to the problem of removing such bromo-aromatic impurities from phthalic anhydride. It might be thought that said bromo-aromatic impurities would be removed by heating such impure anhydride to and/or above its boiling temperature in the absence or in the presence of alkali metal hydroxide or phthalate according to U.S. Pat. No. 2,670,325 to decrease color and odor formers or according to copending U.S. patent application Ser. No. 898,930 filed Apr. 24, 1978 to decrease phthalide content. However, such heating of the anhydride at from 250° C. up to 280° C. for up to four hours in the presence of alkali metal hydroxides and phthalates do not decrease the anhydride's bromine content below about 30 weight parts per million weight parts of the anhydride. Also heating such anhydride at 250° C. for 2 hours in the presence of debrominators zinc or iron suggested by U.S. Pat. No. 3,642,883 did not decrease the bromine content below 30 ppm.

We provide hereafter demonstrations of the ineffectiveness of the prior art described and suggested processes for purification of phthalic acid, phthalic anhydride and removal of bromine from organic compounds in general.

To better understand the advance of the present inventive contribution for decreasing the bromine content of partially purified phthalic anhydride data are presented concerning the starting impure phthalic anhydride, further purification thereof according to some prior art methods used with phthalic anhydride or with other compounds (e.g., bromine removal from benzoic acid with zinc) and an attempt at bromine removal by only activated carbon. Examples of the use of such prior art described or suggested processes for bromine removal are presented in the Comparative Examples to follow wherein "PAN" is used to designate phthalic acid anhydride.

TABLE I
BROMINE REMOVAL FROM PARTIALLY PURIFIED PAN OF 91 PPM BROMINE CONTENT

| Comparative Example No | Heat Treatment at 250° C. for 2 Hours and Addition Agent | PAN Product of Fractionation at 0.13 Atmos. Pressure | |
|---|---|---|---|
| | | Reflux Ratio | Bromine, ppm |
| 1 | None | 1:1 | 82 |
| 2 | K-Biphthalate | 1:1 | 66 |

TABLE II
BROMINE REMOVAL FROM PARTIALLY PURIFIED PAN

| Comparative Example No. | Heat Treatment at 250° C. for 2 Hours and Addition Agent | PAN Product of Fractionation at 0.13 Atmos. Pressure | |
|---|---|---|---|
| | | Reflux Ratio | Bromine, ppm |
| 3 | None | 1:1 | 67 |
| 4 | Zinc | 1:1 | 58 |
| 5 | Pd/C | 1:1 | 32 |

TABLE III
BROMINE REMOVAL FROM PARTIALLY PURIFIED PAN

| Comparative Example No. | Heat Treatment at 250° C. for 2 Hours and Addition Agent | PAN Product of Fractionation at 0.13 Atmos. Pressure | |
|---|---|---|---|
| | | Reflux Ratio | Bromine, ppm |
| 6 | None | 3:1 | 63 |
| 7 | Na-Phthalate | 5:1 | 31 |
| 8 | K-Phthalimide | 5:1 | 36 |
| 9 | K-Biphthalate | 5:1 | 44 |

The use of sodium and potassium salts (Comparative Examples 2, 7, 8 and 9) as additive for the step of heat treating partially purified phthalic anhydride is not any more effective with respect to bromine removal than the use of Pd/C in such step.

The use of catalytic hydrogenation of similar impure phthalic anhydride or bromo-impurities per se is not, as the following data will demonstrate, effective for removing bromine from partially phthalic anhydride. In TABLE IV to follow, three differently supported palladium catalysts: Pd dispersed on the surface of activated carbon (Pd/C), Pd dispersed on alumina (Pd/Aa) and Pd dispersed on chromia-alumina (Pd/Cra-Aa), are used at a hydrogen partial pressure of 0.1 atmosphere and reflux temperature (275° C.) of partially purified PAN (hereafter "Reflux" Process) or at a hydrogen partial pressure of 6.7 atmospheres and a temperature of 299° C. (hereinafter "299° C." Process). The partially purified, liquid PAN was caused to flow through a bed of the catalyst used. A sample of the partially purified PAN is taken before catalytic hydrogenation (0 hr.), and at 0.5 hr., 1.0 hr., and 2.0 hr. after start of such treatment.

TABLE IV
COMPARATIVE CATALYTIC HYDROGENATION FOR BROMINE REMOVAL

| Example No. | Product | PAN's Bromine Content, wt. % | |
|---|---|---|---|
| | | Catalyst | Process |
| 11 | PAN | Pd/C | 299° C. |
| 12 | PAN | Pd/Cra-Aa | Reflux |
| 13 | Br-BA* | Pd/C | 299° C. |
| 14 | Br-BA | Pd/Cra-Aa | 299° C. |
| 15 | Br-BA | Pd/C | Reflux |
| 16 | Br-BA | Pd/Aa | Reflux |
| 17 | Br-BA | Pd/Cra-Aa | Reflux |

*"Br-BA" is bromo-benzoic acid.

| Example No. | PAN's Bromine Content, wt. % | | | |
|---|---|---|---|---|
| | 0 hr. | 0.5 hr. | 1.0 hr. | 2.0 hr. |
| 11 | 0.16 | 0.18 | 0.17 | 0.16 |
| 12 | 0.047 | N.S.* | 0.043 | 0.042 |
| 13 | 0.10 | 0.07 | 0.05 | 0.04 |
| 14 | 0.10 | 0.06 | 0.05 | 0.03 |
| 15 | 0.10 | 0.08 | 0.07 | 0.06 |
| 16 | 0.10 | 0.08 | 0.07 | 0.06 |
| 17 | 0.09 | 0.06 | 0.06 | 0.05 |

*"N.S." is No Sample analyzed.

The heat treating of partially purified PAN is conducted at temperatures of 200° C., 250° C., and 275° C. for four hours in the presence of 0.28 wt.% KOH as additive or no additive (NONE) and thereafter fractionally distilled at a pressure of 0.13 atmosphere to remove a benzoic acid-containing first fraction and then to remove a PAN product fraction. The bromine content of the feed and of the resulting products are shown below in TABLE V.

TABLE V

| Comparative Example No. | Heat Treatment | | Bromine Content, ppm | |
|---|---|---|---|---|
| | Additive | Temp. °C. | Feed | Product |
| 18 | KOH | 200 | 1074 | 128 |
| 19 | NONE | 200 | 1055 | 116 |
| 20 | KOH | 250 | 885 | 68 |
| 21 | NONE | 250 | 950 | 80 |
| 22 | KOH | 275 | 692 | 30 |
| 23 | NONE | 275 | 772 | 38 |

We have now discovered a technique for removing the bromine content of phthalic anhydride contributed by the bromine and oxygen-substituted aromatic compounds before or after, preferably before, heating the impure anhydride at or above its boiling point temperature. Such technique is practiced on phthalic anhydride in the vapor phase and can be conveniently conducted with the anhydride vaporized from the dehydration of o-phthalic acid, or vaporized from the heating step generally also used to condense color bodies and color formers to higher boiling products or vaporized in the final purification of the anhydride by fractional distillation.

STATEMENT OF THE INVENTION

The bromine content of partially purified phthalic anhydride obtained as before described can be diminished to less than 3 ppm by weight based on the anhydride by contacting the vapors of such partially purified anhydride and a small amount of water vapor with a particulated solid catalyst comprising from 0.01 up to 10 weight percent, preferably 0.1 to 1.0 weight percent, metallic palladium or platinum disposed on the surface of carbon or charcoal (hereafter Pd/C or Pt/C). Such carbon or charcoal is known as activated carbon. Suitably such activated carbon has a surface area to mass ratio of at least 100 and up to 3000 m²/g, preferably from 500 to 2000 m²/g.

Such contact treatment is of short duration, merely passing the vapors of the partially purified phthalic anhydride through a short bed of such particulated catalyst will provide a sufficient contact time for the practice and the purposes of this invention.

It is indeed surprising that merely contacting the vapors of the partially purified phthalic anhydride and small amount of water vapor with the Pd/C or Pt/C catalyst in the absence of hydrogen can effect the debromination to a concentration of less than 3 ppm by weight of the anhydride.

The limit of the X-ray fluorescence detection analytical technique to detect bromine in a composition containing phthalic anhydride is 3 weight part of bromine per $1.0 \times 10^6$ (million) weight parts of the anhydride, i.e., 0.0003 wt.%. Thus "less than 3 ppm by weight of bromine based on the anhydride" means no detectable bromine.

In these Examples the previous designations for activated carbon (C), palladium on carbon (Pd/C) and PAN for phthalic anhydride are again used.

As demonstrated, the treatment of liquid partially purified PAN with hydrogen and Pd/C catalyst does not effectively cause debromination of the bromoaromatic impurity: ArBr, according to the equation

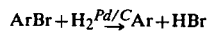

However, when water vapor is present, effective debromination of the aromatic impurity (ArBr) possibly occurs in the presence of Pd/C catalyst according to the equation

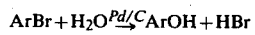

Thus the presence of a "small amount" of water with partially purified PAN would be a quantity of water at least equal to 0.25 times the weight percent of bromine present. Greater quantities of water, for example, up to 20 weight percent of the mixture of PAN and water can be contacted with the Pd/C catalyst without diminishing the debromination effectiveness.

EXAMPLES I–III

The reaction effluent from the neat oxidation of o-xylene with air to o-phthalic acid in the presence of catalysis provided by ions of Co, Mn and Br is diluted with water to a water content of 20 weight percent and held as a fluid at a temperature of 200° C. at a pressure of 10.2 kg/cm² as feed for dehydration of its o-phthalic acid content (72 weight percent) and evaporation of phthalic anhydride and materials boiling lower than phthalic anhydride. Such feed is dehydrated between the temperatures of 198° C. and 210° C. in a thin film evaporator having an evaporation surface of 929 cm² area operated at a subatmospheric pressure of 0.13 atmosphere. About one-half of the vapor mixture so generated is passed through a vertical tube loosely packed with 125 grams of activated carbon and then through a condenser cooled to 135° C. to condense phthalic anhydride. The remaining one-half of the generated vapor mixture is first passed through a tube Pd/C particulate catalyst having 0.5 weight percent palladium dispersed on an activated carbon carrier and then through the condenser operated at the temperature of 135° C. The two differently treated condensates are separately collected. The condensate whose vapors were treated with only activated carbon in the presence of water vapor is divided into two equal samples: Sample A and Sample B. The condensate whose vapors were treated with Pd/C in the presence of water vapor is also divided into two equal samples: Sample C and Sample D.

Each Sample is heat treated, that is heated to and maintained at a temperature of either 250° C. (Samples A, C and D) or 300° C. (Sample B) and then subjected to batchwise fractionation in a 20 tray Oldershaw distillation column at a subatmospheric pressure of 0.13 atmosphere. In each fractionation a 5 weight percent first fraction of low boiling materials is taken at a reflux ratio of 50 to 1. Thereafter the PAN product fractions are taken at the reflux ratio shown. The PAN products so obtained are analyzed by X-ray fluorescence for bromine content. The results of the foregoing processes are shown in TABLE VI.

TABLE VI

Bromine Removal From Partially Purified PAN By Contact of Its Vapors and Water Vapor With Activated Carbon or Palladium Dispersed on Activated Carbon

| Sample | Heat Treat., hr. | PAN Product Reflux Ratio | Bromine Content, wt. % |
|---|---|---|---|
| A | 2 | 3:1 | 0.0063 |
| B | 2 | 5:1 | 0.0018 |
| C | 2 | 1:1 | 0.0032 |
| D | 64 | 5:1 | 0.0003 |

The treatment of Samples C and D above, prior to heat treatment and fractionation constitute one method of practicing the present invention and are Examples I and II.

Another method for the practice of the present invention is described in Examples III and IV to follow.

EXAMPLE III

A fluid reaction effluent, 1482.5 grams, is combined with 370.5 grams of water and is heated to and maintained at 200° C. under a gauge pressure of 15.5 kg/cm². The fluid reaction effluent contains 88.8 weight percent o-phthalic anhydride and 0.31 weight percent bromine (from organic and inorganic bromides). Such fluid effluent is from the neat oxidation of liquid o-xylene with air in the presence of catalysis provided by ions of Co, Mn and Br. Said hot, pressurized, diluted, fluid effluent is fed to a dehydrator evaporator operated at a temperature of 198° C. and a subatmospheric pressure of 0.053 atmospheres. The recovered partially purified PAN (condensed at 130° C.) contains 85.8 phthalic anhydride and has a bromine content (from organo-aromatic compounds) of 0.61 weight percent.

The partially purified PAN is heated at a temperature of 275° C. in the presence of 0.14 weight percent potassium hydroxide for 2 hours and then fractionated at 0.15 atmosphere. A first fraction of about 3 weight percent is taken at a reflux ratio of 50:1 to remove low boiling (lower than PAN) materials. Product PAN is taken at a 1:1 reflux ratio. The product PAN vapors are passed through a column (also operated at 0.15 atmosphere pressure) packed with a particulate catalyst comprising 0.35 wt.% Pd dispersed on activated carbon. Steam in an amount of 0.2 weight percent of the phthalic anhydride is injected into the product PAN vapors as they enter the catalyst bed. Product PAN is condensed at 135° C. Product PAN can be recovered in this manner having a bromine content of less than 0.0003 weight percent.

EXAMPLE IV

A fluid feed containing 65.5 weight percent o-phthalic acid, 17 weight percent water and 0.5 weight percent bromine from organic and inorganic bromides. Said feed comprises water diluted fluid reaction effluent from a continuous neat oxidation of liquid o-xylene in the presence of the Co-Mn-Br system of catalysis. Such feed is maintained at a temperature of 200° C. and a gauge pressure of 10.2 kg/cm² and is fed to a dehydration and evaporation zone having a heated (210° C. to 230° C.) film surface area of 929 cm² operated under a subatmospheric pressure of from 0.12 up to 0.145 atmosphere at the rate of 31.2 grams per minute. The mixture of water and PAN vapors discharged from such dehydration-evaporation is cooled to 135° C. to selectively condense PAN as a liquid and permit water vapor to be discarded. The partially purified PAN condensate is heated to 277° C. under reflux conditions in the presence of 0.32 weight percent potassium hydroxide for four hours and is then fractionated at subatmospheric pressure of 0.13 atmosphere.

A PAN product fraction when treated as a vapor with 0.5 weight percent palladium on activated carbon with steam injected at 3 to 5 weight part per weight part of PAN, can be recovered by condensation at a temperature at which steam does not condense at subatmospheric pressure of 0.13 atmosphere. PAN condensate so obtained and recovered can have a molten color stability (ASTM Test Method D1209-69) of about 10 (APHA color Pt-Co scale) and a bromine content of less than 0.0003 weight percent.

The invention claimed is:

1. For the method of purification of phthalic anhydride having bromine-containing compounds as impurities wherein such phthalic anhydride is fractionally distilled to obtain a purified phthalic anhydride product fraction, the improvement comprising contacting vapors of water and phthalic anhydride with particulated solid catalyst comprising palladium or metal disposed on activated carbon prior to vapors of phthalic anhydride being taken as the product fraction.

2. The method of claim 1 wherein the contacting of vapors of water and phthalic anhydride with the Pd disposed on activated carbon occurs prior to fractionation of said anhydride.

3. The purification method of claim 1 which comprises vaporizing phthalic anhydride afterit has been heat treated in the liquid phase at a temperature of from 200° C. up to 300° C. and contacting said vapor of phthalic anhydride and water vapor with particulated solid catalyst comprising Pd metal disposed upon the surface of activated carbon.

4. The method of claim 3 wherein the contacting of water and phthalic anhydride vapors with the Pd metal disposed on activated carbon occurs with phthalic anhydride product fraction vapors.

5. The method of claim 1 wherein the vapors of water and phthalic anhydride are obtained by dehydration of o-phthalic acid having bromine-containing impurities and such vapors are contacted with Pd disposed on activated carbon following said dehydration of o-phthalic acid.

* * * * *

UNITED STATES PATENT OFFICE
CERTIFICATE OF CORRECTION

Patent No. 4,197,247  Dated April 8, 1980

Inventor(s) Hobe Schroeder and Delbert H. Meyer

It is certified that error appears in the above-identified patent and that said Letters Patent are hereby corrected as shown below:

The Patent Reads:

| Col. | Line | | | | |
|---|---|---|---|---|---|
| 1 | 51 | "do" | and should read | --does-- |
| 2 | 54 | "partially phthalic" | " " | " | --partially purified phthalic-- |
| 2 | 63 | "(hereinafter)" | " | " | --(hereafter)-- |
| 3 | 30 | "are" | " | " | --is-- |
| 4 | 45 | "EXAMPLES I-III" | " | " | --EXAMPLES I-II-- |
| 5 | 51 | "85.8 phthalic anhydride" | " | " | --85.8 weight percent phthalic anhydride-- |
| 6 | 51 | "afterit" | " | " | --after it-- |

Signed and Sealed this

Seventh Day of October 1980

[SEAL]

Attest:

SIDNEY A. DIAMOND

Attesting Officer  Commissioner of Patents and Trademarks

UNITED STATES PATENT OFFICE
CERTIFICATE OF CORRECTION

Patent No. 4,197,247   Dated April 8, 1980

Inventor(s) Hobe Schroeder and Delbert H. Meyer

It is certified that error appears in the above-identified patent and that said Letters Patent are hereby corrected as shown below:

Front Page

After paragraph beginning "Inventors:..." please insert new paragraph to read:

"Assignee: Standard Oil Company, (Indiana), Chicago, Ill.

Signed and Sealed this

Twenty-seventh Day of September 1983

[SEAL]

Attest:

GERALD J. MOSSINGHOFF

Attesting Officer   Commissioner of Patents and Trademarks